(12) United States Patent
Johnson

(10) Patent No.: US 10,407,387 B2
(45) Date of Patent: *Sep. 10, 2019

(54) METHOD FOR MAKING N-(FLUOROSULFONYL) DIMETHYLAMINE

(71) Applicant: TRINAPCO, INC., Oakland, CA (US)

(72) Inventor: Martin Reid Johnson, Piedmont, CA (US)

(73) Assignee: Trinapco, Inc., Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/138,656

(22) Filed: Sep. 21, 2018

(65) Prior Publication Data
US 2019/0023653 A1    Jan. 24, 2019

Related U.S. Application Data

(63) Continuation of application No. 15/816,719, filed on Nov. 17, 2017, now Pat. No. 10,106,495.

(60) Provisional application No. 62/489,844, filed on Apr. 25, 2017, provisional application No. 62/424,392, filed on Nov. 19, 2016.

(51) Int. Cl.
*C07C 303/34* (2006.01)

(52) U.S. Cl.
CPC ................. *C07C 303/34* (2013.01)

(58) Field of Classification Search
None
See application file for complete search history.

(56) References Cited

U.S. PATENT DOCUMENTS 2,130,038 A    9/1938  Schrader et al.
10,106,495 B2 * 10/2018 Johnson ............ C07C 303/34

FOREIGN PATENT DOCUMENTS

| CA | 2321373 A1 | 3/2001 |
| CN | 1289765 A  | 4/2001 |
| DE | 667544 C   | 11/1938 |

(Continued)

OTHER PUBLICATIONS

Sakuth ("Ethers, Aliphatic" Ullmann's Encyclopedia of Industrial Chemistry, 2010, p. 433-449, downloaded from https://doi.org/10.1002/14356007.a10_023.pub2) on Feb. 19, 2019) (Year: 2010).*

(Continued)

*Primary Examiner* — Amy C Bonaparte
(74) *Attorney, Agent, or Firm* — Duane Morris LLP

(57) ABSTRACT

Dimethylamine ($Me_2NH$) is reacted with sulfuryl fluoride ($SO_2F_2$) to form at least a first phase comprising N-(fluorosulfonyl) dimethylamine ($FSO_2NMe_2$), tetramethylsulfamide ($SO_2(NMe_2)_2$), or a combination thereof. A second phase, which may include dimethylamine hydrofluoride ($Me_2NH_2F$), may be also formed and separated from the first phase. $FSO_2NMe_2$ or $SO_2(NMe_2)_2$ is then isolated from the first phase. For example, the first phase may be a liquid phase, and $FSO_2NMe_2$ and $SO_2(NMe_2)_2$ are separated by distillation, optionally under reduced pressure.

13 Claims, 1 Drawing Sheet

(56) References Cited

FOREIGN PATENT DOCUMENTS

| | | | |
|---|---|---|---|
| DE | 1493486 | * | 11/1969 |
| DE | 1943233 | A1 | 3/1971 |
| FR | 806383 | A | 12/1936 |
| GB | 1264774 | A | 2/1972 |
| WO | 2015188120 | A1 | 12/2015 |

OTHER PUBLICATIONS

SciFinder entry for N,N,N',N'-tetramethylsulfamide, downloaded on Feb. 19, 2019 (Year: 2019).*

Heap, R., et al., "Esters Containing Phosphorus. Part VII. Substituted Diaminofluorophosphine Oxides" Journal of the Chemical Society (Resumed), 1948, 1313-1316.

Appel, R. et al., "Additionsreaktionen von N, N-Dialkylsulfamiden, tertiaren Aminen and Phosphinen mit Fluorsulfonylisocyanat" Chemische Berichte, 1977, 110, 2368-2373 [English summary included].

Guo, T. et al., "A New Portal to SuFEx Click Chemistry: A Stable Fluorosulfuryl Imidazolium Salt Emerging as an "F-SO2+" Donor of Unprecedented Reactivity, Selectivity, and Scope" Jan. 25, 2018, Angew. Chem. Int. Ed., John Wiley & Sons, Ltd, 7 pages.

Emeleus ("The Preparation and Reactions of Carbonyl and Sulphuryl Fluorides and Chlorofluorides" Journal of the Chemical Society, 1948, p. 2183-2188) (Year: 1948).

Diethylamine (Sigma Alrich data sheet for diethylamine, p. 1-6, downloaded from https://www.sigmaaldrich.com/catalog/product/sial/471216?lang=en&region=US on Jan. 16, 2018) (Year: 2018).

Diethyl Ether (Sigma Aldrich data sheet for diethyl ether, downloaded from https://www.sigmaaldrich.com/catalog/product/sial/296082?lang=en&region=US on Jan. 20, 2018, p. 1-6) (Year: 2018).

Leonard ("chapter ten: Working up the reaction" Advanced Practical Organic Chemistry, p. 191-208, 2010) (Year: 2010).

Dichloromethane (Sigma Aldrich data sheet for dichloromethane, downloaded from https://www.sigmaaldrich.com/chemistry/solvents/dichloromethane-center.html on Jan. 20, 2018, p. 1-2) (Year 2018).

Padma ("Reactions of sulphuryl fluoride, sulphuryl chlorofluoride and sulphuryl chloride with amines" Journal of Fluorine Chemistry, vol. 20, p. 425-437, 1982) (Year: 1982).

\* cited by examiner

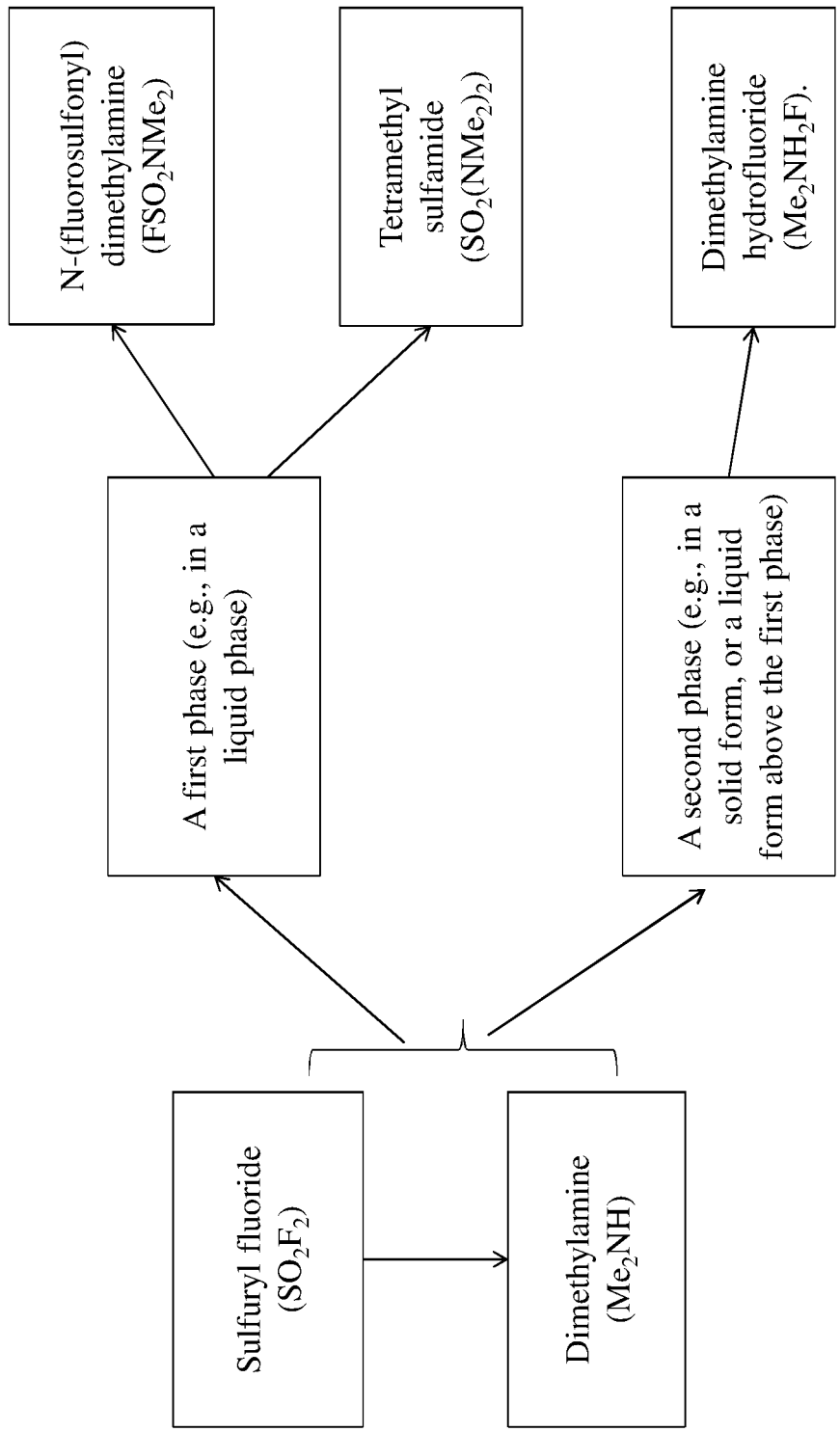

US 10,407,387 B2

METHOD FOR MAKING N-(FLUOROSULFONYL) DIMETHYLAMINE

PRIORITY CLAIM AND CROSS-REFERENCE

This application is a continuation application of U.S. application Ser. No. 15/816,719, filed Nov. 17, 2017, which claims the benefit of U.S. Provisional Application No. 62/424,392, filed Nov. 19, 2016, and U.S. Provisional Application No. 62/489,844, filed Apr. 25, 2017. These provisional and nonprovisional applications are expressly incorporated by reference herein in their entireties.

FIELD OF THE INVENTION

The disclosure relates to chemical synthesis generally. More particularly, the disclosed subject matter relates to a method for preparing a tertiary amide of fluorosulfonic acid, and related derivatives.

BACKGROUND

The compound N-(fluorosulfonyl) dimethylamine ($FSO_2NMe_2$) has been proposed as a solvent or additive for lithium-ion batteries (Chinese Patent No. CN 1 289 765A). Ai present. $FSO_2NMe_2$ is not commercially available in large amounts.

$FSO_2NMe_2$ was first prepared in the 1930s by metathesis between N-chlorosulfonyl dimethylamine ($ClSO_2NMe_2$) and potassium, sodium, or zinc fluoride in water (French Patent No. FR 806 383; German Patent No. DE 667 544; U.S. Pat. No. 2,130,038).

$FSO_2NMe_2$ has also been prepared by the reaction of $ClSO_2NMe_2$ with antimony trifluoride ($SbF_3$) in the presence of antimony pentafluoride ($SbF_5$) (Heap, R., Saunders, B. C., *Journal of the Chemical Society (Resumed)*, 1948, 1313-1316), and by the reaction of $ClSO_2NMe_2$ with anhydrous HF at 80-90° C. (German Patent No. DE 1 943 233 (1971)).

$FSO_2NMe_2$ has also been prepared by the reaction of N,N-dimethylaminosulfamide ($Me_2NSO_2NH_2$) with fluorosulfonyl isocyanate ($FSO_2N=C=O$) at 80° C. (Appel, R.; Montenarh, M., *Chemische Berichte*, 1977, 110, 2368-2373).

There are four known examples of the reaction of sulfuryl fluoride ($SO_2F_2$) with secondary amines as described below. The four known reactions employ cryogens (or catalysts). But the reaction of dimethylamine ($Me_2NH$) with $SO_2F_2$ is not known yet.

The reaction of $SO_2F_2$ with a secondary amine was first performed in 1948 (Emeléus, H. J., Wood, J. F., *Journal of the Chemical Society (Resumed)*, 1948, 2183-2188). In this paper, diethylamine ($Et_2NH$) was dropped into a cooled (−78° C.) solution of $SO_2F_2$ in ethyl ether, and the product, $FSO_2NEt_2$, was obtained in a yield of 35%.

The reaction of $SO_2F_2$ with piperidine ($HN(CH_2)_5$) was performed in 1982 (Padma, D. K., Subrahmanya Bhat, V., Vasudeva Murthy, A. R., *Journal of Fluorine Chemistry*, 1982, 20, 425-437). $SO_2F_2$ was added into piperidine in ether at liquid nitrogen temperatures, followed by warming. Either $FSO_2N(CH_2)_5$ or $SO_2(N(CH_2)_5)_2$ was obtained depending on the amount of piperidine used.

The reaction of two more secondary amines with $SO_2F_2$, under ambient conditions, is described in a patent application by Dong and Sharpless (International Patent Application No. WO 2015/188120). In this application, diallyl amine and dipropargyl amine react with $SO_2F_2$ in the presence of an equivalent of an activating agent in a solvent. The solvents such as tetrahydrofuran (THF) and dichloromethane were particularly described (page 58, line 15). Dong and Sharpless asserted that "activated amines can even react in buffer at pH 8" (page 95, line 14), but gave no examples of activated amines, and did not further elaborate.

There is a need for a process for synthesis of N-(fluorosulfonyl) dimethylamine, which is safely and economically scaled up for commercial production.

SUMMARY OF THE INVENTION

The present disclosure provides a method for preparing chemicals. In accordance with some embodiments, such a method comprises reacting dimethylamine ($Me_2NH$) with sulfuryl fluoride ($SO_2F_2$) to form at least a first phase comprising N-(fluorosulfonyl) dimethylamine ($FSO_2NMe_2$), tetramethylsulfamide ($SO_2(NMe_2)_2$), or a combination thereof, and isolating $FSO_2NMe_2$ or $SO_2(NMe_2)_2$ from the first phase. The first phase may be a liquid phase. Isolating $FSO_2NMe_2$ or $SO_2(NMe_2)_2$ comprises a step of distilling the first phase, optionally under a reduced pressure.

In some embodiments, the method further comprises separating a second phase from the first phase after $Me_2NH$ is reacted with $SO_2F_2$. The second phase comprises dimethylamine hydrofluoride ($Me_2NH_2F$). When $Me_2NH$ is reacted with $SO_2F_2$ in the absence of a solvent added or in a solvent with a limited solubility for $Me_2NH_2F$, and the second phase is a solid phase. When $Me_2NH$ is reacted with $SO_2F_2$ in a solvent (or mixture) comprising water or a solvent having good solubility for $Me_2NH_2F$, and the second phase is a liquid phase. $Me_2NH_2F$ may be isolated from the second phase.

The inventor has found that $SO_2F_2$ reacts with $Me_2NH$, with or without added solvent, to form $FSO_2NMe_2$, dimethylammonium fluoride ($Me_2NH_2F$) and tetramethylsulfamide ($SO_2(NMe_2)_2$). In some embodiments, $FSO_2NMe_2$ is the desired product, while $Me_2NH_2F$ and $SO_2(NMe_2)_2$ are byproducts. In some embodiments, either or both of $SO_2(NMe_2)_2$ and $Me_2NH_2F$ may be also desired products. In some embodiments, when the byproduct $Me_2NH_2F$ is desired as a solid, the reaction can be performed in a solvent which does not dissolve $Me_2NH_2F$, and the solid byproduct is collected by filtration. In some other embodiments, when the byproduct $Me_2NH_2F$ is not desired as a solid, the reaction can be performed in other solvents, for example, water, in which the byproduct can be dissolved.

In accordance with some embodiments, a method comprises reacting dimethylamine ($Me_2NH$) with sulfuryl fluoride ($SO_2F_2$) in the presence of a solvent to form at least a first phase, which is a liquid phase comprising N-(fluorosulfonyl) dimethylamine ($FSO_2NMe_2$), and isolating $FSO_2NMe_2$ from the first phase. The first phase may optionally comprise tetramethylsulfamide ($SO_2(NMe_2)_2$). The method further comprises separating a second phase from the first phase after $Me_2NH$ is reacted with $SO_2F_2$. The second phase comprises dimethylamine hydrofluoride ($Me_2NH_2F$), and may be a solid or liquid phase. In some embodiments, $FSO_2NMe_2$ is isolated by distilling the first phase under a reduced pressure.

Examples of a suitable solvent include, but are not limited to, methanol, ethanol, water, dichloromethane, ethyl ether, tetrahydrofuran, 2-methyltetrahydrofuran, methylcyclopentyl ether, methyl tert-butyl ether, acetonitrile, propionitrile, butyronitrile, toluene, and any combination thereof. In some embodiments, the solvent comprises water, for example, water, or a mixture comprising water and another solvent. In some embodiments, $Me_2NH$ is reacted with $SO_2F_2$ at a molar ratio of $Me_2NH$ to $SO_2F_2$ in a range of from about 0.1:1 to about 4:1. The reaction of $Me_2NH$ with $SO_2F_2$ may be conducted at a temperature, for example, in a range from about −30° C. to about 110° C.

In accordance with some embodiments, a method comprises reacting dimethylamine ($Me_2NH$) with sulfuryl fluoride ($SO_2F_2$) in the presence of water to form at least a first phase, which is a liquid phase comprising N-(fluorosulfonyl) dimethylamine ($FSO_2NMe_2$), and isolating $FSO_2NMe_2$ from the first phase. The first phase may optionally comprise tetramethylsulfamide ($SO_2(NMe_2)_2$).

The method may further comprise separating a second phase from the first phase after $Me_2NH$ is reacted with $SO_2F_2$. The second phase ("upper layer") is an aqueous solution having a density less than that of the first phase ("lower layer") and comprises dimethylamine hydrofluoride ($Me_2NH_2F$). $FSO_2NMe_2$ can be isolated by distilling the first phase under a reduced pressure. $SO_2(NMe_2)_2$ may be collected from the first phase after distillation under a reduced pressure.

In some embodiments, water is present in any suitable amount, for example, in the range of from about 35% to about 80% by weight in a total weight of water and dimethylamine, before $SO_2F_2$ is added. The molar ratio of $Me_2NH$ to $SO_2F_2$ is in a range of from about 0.1:1 to about 4:1, for example, from about 2.00:1 to about 2.09:1. The molar ratio of $Me_2NH$ to $SO_2F_2$ is higher than 2.1:1, or even higher than 4:1 in some embodiments. In some embodiments, $Me_2NH$ is reacted with $SO_2F_2$ at a temperature between −30° C. and about 110° C., for example, between −15° C. and about 60° C. The reaction of $Me_2NH$ with $SO_2F_2$ can be performed in a reactor in a batch process, or a continuous process.

In some embodiments, when the reaction is performed in water, $FSO_2NMe_2$ is obtained in yields as high as 97%. The reaction in water has been performed at a temperature in the range of from −28° C. to +106° C., at water levels from 0% to 77% w/w, and at pressures from below atmospheric up to 1.4 MPa. For reactions conducted in water, a molar ratio of $Me_2NH$ to $SO_2F_2$ of 2.01:1 is preferred. For reactions conducted in water below atmospheric pressure, an aqueous solution of $Me_2NH$ at a water concentration in the range of 35-60 wt. % (i.e. a concentration of water in the total weight of water and $Me_2NH$), and a pot temperature of −15° C. to +45° C. are preferred, and a yield of 75-96% is obtained. For reactions conducted in water above atmospheric pressure, an aqueous solution of $Me_2NH$ at a water concentration in the range of 40-80 wt. %, and a temperature of 10° C. to 50° C. are preferred, and a yield of up to 97% is obtained. When sufficient water is present, nearly pure product separates as a lower layer, which is drawn off and distilled to give the pure product, and can be performed as a continuous process. An aqueous continuous process is preferred in some embodiments.

BRIEF DESCRIPTION OF THE DRAWINGS

The present disclosure is best understood from the following detailed description when read in conjunction with the accompanying drawings. It is emphasized that, according to common practice, the various features of the drawings are not necessarily to scale. On the contrary, the dimensions of the various features are arbitrarily expanded or reduced for clarity. Like reference numerals denote like features throughout specification and drawings.

FIG. 1 is a diagram illustrating an exemplary process in accordance with some embodiments.

DETAILED DESCRIPTION

For purposes of the description hereinafter, it is to be understood that the embodiments described below may assume alternative variations and embodiments. It is also to be understood that the specific articles, compositions, and/or processes described herein are exemplary and should not be considered as limiting.

In the present disclosure the singular forms "a," "an," and "the" include the plural reference, and reference to a particular numerical value includes at least that particular value, unless the context clearly indicates otherwise. When values are expressed as approximations, by use of the antecedent "about," it will be understood that the particular value forms another embodiment. As used herein, "about X" (where X is a numerical value) preferably refers to ±10% of the recited value, inclusive. For example, the phrase "about 8" preferably refers to a value of 7.2 to 8.8, inclusive; as another example, the phrase "about 8%" preferably (but not always) refers to a value of 7.2% to 8.8%, inclusive. Where present, all ranges are inclusive and combinable. For example, when a range of "1 to 5" is recited, the recited range should be construed as including ranges "1 to 4", "1 to 3", "1-2", "1-2 & 4-5", "1-3 & 5", "2-5", and the like. In addition, when a list of alternatives is positively provided, such listing can be interpreted to mean that any of the alternatives may be excluded, e.g., by a negative limitation in the claims. For example, when a range of "1 to 5" is recited, the recited range may be construed as including situations whereby any of 1, 2, 3, 4, or 5 are negatively excluded; thus, a recitation of "1 to 5" may be construed as "1 and 3-5, but not 2", or simply "wherein 2 is not included." It is intended that any component, element, attribute, or step that is positively recited herein may be explicitly excluded in the claims, whether such components, elements, attributes, or steps are listed as alternatives or whether they are recited in isolation.

Sulfuryl fluoride is bifunctional, and both fluoride atoms are reactive, especially towards dimethylamine, one of the least sterically hindered of all the secondary amines. The reaction of dimethylamine ($Me_2NH$) with $SO_2F_2$ is not known yet. Even if such a reaction would exist, it was not clear that a set of noncryogenic conditions could exist, in which $FSO_2NMe_2$ was the dominant product or even isolable after a reaction of $Me_2NH$ with $SO_2F_2$. These conditions have now been established in the present Invention.

The present disclosure provides a method for preparing N-(fluorosulfonyl) dimethylamine ($FSO_2NMe_2$) and/or tetramethylsulfamide ($SO_2(NMe_2)_2$). Referring to FIG. 1, in accordance with some embodiments, an exemplary method comprises reacting dimethylamine ($Me_2NH$) with sulfuryl fluoride ($SO_2F_2$) to form at least a first phase comprising N-(fluorosulfonyl) dimethylamine ($FSO_2NMe_2$), tetramethylsulfamide ($SO_2(NMe_2)_2$), or a combination thereof. $FSO_2NMe_2$ and/or $SO_2(NMe_2)_2$ is isolated from the first phase. The first phase may be a liquid phase. Isolating $FSO_2NMe_2$ and/or $SO_2(NMe_2)_2$ comprises a step of distilling the first phase, optionally under a reduced pressure. The method may further comprise separating a second phase from the first phase after $Me_2NH$ is reacted with $SO_2F_2$. The second phase comprises dimethylamine hydrofluoride ($Me_2NH_2F$).

Referring to FIG. 1, when $Me_2NH$ is reacted with $SO_2F_2$ without a solvent or in a solvent with a limited solubility for $Me_2NH_2F$, the second phase is a solid phase. Unless expressly indicated otherwise, reference to "limited solubility" made herein means a solubility of a solute in a solvent being 100 mg/L or less (e.g., lower than 10, 5, 1 mg/L). When $Me_2NH$ is reacted with $SO_2F_2$ in a solvent (or mixture) comprising water or a solvent having good solubility for $Me_2NH_2F$, the second phase is a liquid phase.

The present Invention describes the addition of gaseous $SO_2F_2$ to liquid $Me_2NH$, either neat or in solution, to give one or more products selected from $FSO_2NMe_2$, $Me_2NH_2F$ and $SO_2(NMe_2)_2$. In some embodiments of the Invention, $SO_2F_2$ can be added as a solution in a solvent, but these embodiments are less preferred. Of the three products of the present Invention, $FSO_2NMe_2$ is the most valuable and is the preferred product. $FSO_2NMe_2$ is a dense (1.2 g/mL), water-immiscible polar liquid with a low viscosity and liquid range of $-16.7°$ C. to $+149°$ C. $FSO_2NMe_2$ is saturated with 0.475 grams of water per 100 mL of $FSO_2NMe_2$ at 25° C.; this is reduced to about 50 ppm by fractional distillation at atmospheric pressure. Pure $FSO_2NMe_2$ dissolves many uncharged aprotic substrates and is inert to them. Its flash point is above its boiling point: a Bunsen burner held over a boiling beaker of $FSO_2NMe_2$ does not ignite the vapors. Its widespread use has not been adopted.

The present Invention makes possible large-scale production of $FSO_2NMe_2$ at very low cost. The precursors, $SO_2F_2$ and $Me_2NH$, are both inexpensive and available on a metric ton scale. When water is used as the solvent, product $FSO_2NMe_2$ is simply drawn off from the aqueous layer and distilled. The aqueous waste stream in such a process can be treated with lime to recover the fluoride, and then distilled to recover the free $Me_2NH$ thereby produced. By use of an aqueous continuous process, very large amounts of $FSO_2NMe_2$ can be produced using the present Invention, in a short amount of time, with minimal labor.

The present Invention was performed in a temperature range of $-30°$ C. to $+110°$ C. More preferable temperature ranges depend on the process pressure and the type and quantity of solvent employed. These conditions are more clearly elaborated below and in the Examples. The present Invention can be practiced under three types of solvent conditions: with 100% $Me_2NH$ as solvent, with an anhydrous solvent, and with water as part or all of the solvent. The reaction can be performed in an open pot or a sealed pot, more preferably a sealed pot. The present Invention can be performed as a continuous process.

Reaction with Pure Dimethylamine:

In one embodiment of the Invention, the reaction can be performed using an excess amount of liquid $Me_2NH$ as the solvent, under suitable pressure and temperature. $Me_2NH$ has a boiling point of 7-9° C. Due to its low boiling point, $Me_2NH$ is shipped and stored as a liquid under its vapor pressure in a tank. Yields are above 90% (see Example 1).

However, the reaction using liquid $Me_2NH$ as the solvent is less preferred. The main byproduct, $Me_2NH_2F$, congeals as a solid mass, and if solid $Me_2NH_2F$ is desired as a product, it must be chiseled out of the pot. Water may be used to extract the $Me_2NH_2F$, and the liquid streams separated, but in this event it is simpler to use an aqueous solution of $Me_2NH$ as a starting material. $Me_2NH$ is miscible in all proportions with water, and the byproduct $Me_2NH_2F$ is highly soluble in water.

Reaction in Solvent:

In some embodiments of the Invention, a solvent can be used. In some embodiments of the Invention using certain solvents, byproduct $Me_2NH_2F$ can form a suspended solid, which can be filtered off, and the filtrate is distilled to separate $FSO_2NMe_2$ and $SO_2(NMe_2)_2$. In these embodiments of the Invention, protic solvents (methanol, ethanol, and the like), are less preferred, as all three products of the Invention tend to dissolve in protic solvents, and require more labor to separate. Many protic solvents are also known to rapidly react with $SO_2F_2$ in the presence of alkylamines, although the extent of these possible side reactions has not been determined. In some embodiments of the Invention, low-boiling aprotic polar solvents can be used. Examples of such suitable aprotic polar solvents include, but are not limited to, dichloromethane, ethyl ether, tetrahydrofuran, 2-methyltetrahydrofuran, methylcyclopentyl ether, methyl tert-butyl ether, acetonitrile, propionitrile, butyronitrile, toluene, the like, and any combination thereof. Acetonitrile dissolves $SO_2F_2$ quite well and addition performed in this solvent proceeds rapidly at low pressure (See Example 22). However, in acetonitrile, $FSO_2NMe_2$ is quite reactive towards $Me_2NH$ at ambient temperature. In some embodiments of the Invention using solvents other than water, if $FSO_2NMe_2$ is the desired product, the temperature should be low enough (down to as low as the liquidus point of the solvent system), to minimize formation of byproduct $SO_2(NMe_2)_2$. The use of low temperatures incurs cooling costs.

In some embodiments of the Invention, if $FSO_2NMe_2$ is the desired product, anhydrous $Me_2NH$ can be introduced below the surface of the solvent simultaneously with the introduction of $SO_2F_2$ above the surface of the solvent.

In some embodiments of the Invention, the reaction in anhydrous solvent can be conducted entirely below atmospheric pressure.

In some embodiments of the Invention, an anhydrous solvent can be combined with water to create an aqueous solvent.

In some embodiments of the Invention, a water-immiscible anhydrous solvent can be combined with water to create a biphasic solvent system.

Reaction in Water:

In some embodiments of the Invention, water alone is used as a solvent. As used herein, the term "in water" refers to the use of water alone as the solvent. Water levels from 0.01% w/w to 99.9% w/w, more preferably 35-80% w/w, may be used. As used herein, the term "w/w" refers to weight percent of water in the total weight of the reactants at the start of the reaction, with the remaining weight percent being dimethylamine. For example, a 60% w/w aqueous solution consists of 60 wt. % of water and 40 wt. % of dimethylamine. Water readily dissolves both $Me_2NH$ and $Me_2NH_2F$. Uniquely among most likely all secondary amines, the byproduct ($Me_2NH_2F$) is insoluble in the main product ($FSO_2NMe_2$), or at least migrates completely into the aqueous phase. Furthermore, when sufficient water is present, the process stream forms a biphasic liquid without emulsion. For these reasons, water is one of the most preferred solvents in some embodiments.

In some embodiments, the reaction is conducted in water, and the lower layer of $FSO_2NMe_2$ may be separated and distilled without any wash. Furthermore, byproduct $SO_2(NMe_2)_2$ is found in the lower layer only, and is easily separated from $FSO_2NMe_2$ by distillation under reduced pressure. The distillation may be conducted at atmospheric pressure, but cleaner separation is achieved at reduced pressure. Yields of $FSO_2NMe_2$ as high as 97% are obtained. When the Invention is practiced in water, yields of $FSO_2NMe_2$ approaching quantitative are achieved at ambient temperature and above, in contrast to acetonitrile, where substantial byproduct $SO_2(NMe_2)_2$ forms at ambient temperature. When the Invention is practiced in water, power cooling or cryogens are unnecessary. Tap water is cold enough.

Molar Ratio:

The molar ratio of dimethylamine to sulfuryl fluoride is an essential parameter to control when practicing the Invention under both aqueous and nonaqueous conditions. In some embodiments, if $FSO_2NMe_2$ is the desired product, molar ratios ($Me_2NH/SO_2F_2$) of from about 0.1:1 to about 4:1 can be employed, more preferably from 2.00:1 to 2.09:1, most preferably about 2.01:1. In some embodiments, if $SO_2(NMe_2)_2$ is the desired product, molar ratios of 2.5:1 or greater are preferred. In some embodiments of the Invention, molar ratios of greater than 4:1 can be used. Referring to FIG. 1, the diagram is for illustration only. In some embodiments, when the molar ratio of $Me_2NH/SO_2F_2$ is greater than 4:1 and water is used as a solvent, the product is $SO_2(NMe_2)_2$ as a solid, without $FSO_2NMe_2$ in a first liquid phase. Byproduct $Me_2NH_2F$ remains in the aqueous phase.

In some embodiments of the Invention in water, if $FSO_2NMe_2$ is the desired product, molar ratios of 2.1:1 or greater are less preferred. In most of the Examples with a molar ratio of 2.1:1 or greater (e.g., Examples 8, 13, 18, and 20), the yield of product $FSO_2NMe_2$ was less than 90%. The one exception, Example 4, took place at −3° C. and a yield of 94% was obtained.

In some embodiments of the Invention in water, if $FSO_2NMe_2$ is the desired product, molar ratios of 2.00:1-2.09:1 are more preferred. A molar ratio of about 2.01:1 is most preferred. In most of the Examples in water employing the molar ratio of 2.01:1, the yield of $FSO_2NMe_2$ was 95% or greater.

In some embodiments of the Invention in water, if $SO_2(NMe_2)_2$ is the desired product, the molar ratio can be adjusted to allow sufficient $FSO_2NMe_2$ to form in order to dissolve all of the $SO_2(NMe_2)_2$ in the lower layer and thereby enable the process stream to separate as two liquids. The desired product $SO_2(NMe_2)_2$ may then be isolated by distilling off the $FSO_2NMe_2$ from the lower layer, followed by recrystallization from a suitable solvent such as methanol.

In some embodiments of the Invention in water, if $SO_2(NMe_2)_2$ is the desired product, the molar ratio can be 4:1 or higher. In these embodiments of the Invention, product $SO_2(NMe_2)_2$ can separate as a solid.

In some embodiments of the Invention, a tertiary amine such as triethylamine can be added to the pot, or used neat as a solvent, and the molar ratio of $Me_2NH:SO_2F_2$ can be reduced. However, $Me_2NH$ is inexpensive and there is little, if any, cost advantage. The addition of a tertiary amine can add substantial volume and, in a batch process, decrease the pot load. A process stream containing a tertiary amine can require additional process steps. These embodiments of the Invention are less preferred.

Limnic Containment and Eruption Hazard:

In some of the embodiments of the Invention in water, molar ratios of $Me_2NH/SO_2F_2$ below 2:1 are less preferred. For example, embodiments of the Invention conducted in water at molar ratios less than 2:1 are very dangerous and should be practiced only with extra caution. In water at temperatures less than about 100° C., $SO_2F_2$ is not consumed below a molar ratio of 2:1. In water at molar ratios below 2:1, unreacted $SO_2F_2$ concentrates in the dense lower layer, where the partial pressure of $SO_2F_2$ can be contained by the column pressure of the upper layer ("limnic containment"). This can happen despite vigorous agitation and evacuation of the pot (or receptacle in a continuous process), and can create a serious hazard. If the lower layer is directly exposed to atmospheric pressure, vigorous outgassing of highly toxic $SO_2F_2$ can take place ("limnic eruption"). A limnic eruption happened during the course of Example 7. Safety precautions were employed throughout this reaction, and all of the reactions described in the Examples, thus the inventor suffered no ill effects.

In some embodiments of the Invention in water, the reaction can be conducted in an open pot under limnic containment. In these embodiments of the Invention, $SO_2F_2$ is injected below the surface of the pot contents into a dense, water-immiscible solvent such as the product $FSO_2NMe_2$ itself.

In some embodiments of the Invention in water, the reaction can be conducted in a sealed pot under limnic containment. In these embodiments of the Invention, $SO_2F_2$ is injected below the surface of the pot contents into a dense, water-immiscible solvent such as the product $FSO_2NMe_2$ itself, and gaseous $Me_2NH$ introduced to the head space over the aqueous layer.

Temperature:

Another parameter to control when practicing the Invention is the temperature. In water, preferred temperatures can depend on the concentration of water in the pot, the addition time, and the pot pressure. In some embodiments of the Invention in water, if $FSO_2NMe_2$ is the desired product, a temperature from −28° C. to +110° C., more preferably 10-40° C., most preferably 10-30° C., may be employed. In some embodiments, the temperature may be in a range between −15° C. and 60° C. This is illustrated by comparing the Examples with a molar ratio of 2.03:1 or less. Almost all of the Examples below 60° C. with a molar ratio of from 2:1 to 2.03:1 had a yield of 90% or greater, with the highest yields at 40° C. or below. In the Examples below 60° C. with a molar ratio of from 2:1 to 2.03:1, the yield of byproduct $SO_2(NMe_2)_2$ increased as the temperature rose.

In some embodiments of the Invention, if $SO_2(NMe_2)_2$ is the desired product, temperatures of 0-110° C., more preferably 10-60° C., may be employed.

In water at temperatures around 100° C., hydrolysis can occur. One such reaction was performed (Example 21), in an effort to determine the adiabatic temperature rise for the purpose of modeling a continuous process. In this Example, the starting temperature was 12° C. and $SO_2F_2$ was pushed in from a tandem lecture bottle assembly ("tank") as rapidly as possible, taking 8 minutes, until the pot pressure equaled the tank pressure (0.41 MPa). The temperature rose to 106° C. The molar ratio was 1.9:1. The tank was disconnected, the pot cooled to 19° C., and worked up in a manner similar to the other Examples. The aqueous phase of the process stream was acidic, the only such occurrence out of all of the Examples. This indicates that hydrolysis of either the reactant $SO_2F_2$, or products $FSO_2NMe_2$ and $SO_2(NMe_2)_2$, took place during the reaction.

Time:

Two lengths of time are given for each of Examples 1-21: addition time (the time spent adding $SO_2F_2$ to the pot), and total time (from the beginning of addition until the pot is opened). In a continuous process, the total time becomes the "residence time," a term known to those skilled in the art and used hereinafter for both batch and continuous processes. Because these lengths of time are dependent on the type and size of the reactor, the lengths of time given in the Description and Examples are specific to batch process at this scale.

In a batch process in water, if $FSO_2NMe_2$ is the desired product, the addition time is generally more important than the residence time, and should be minimized with a properly cooled pot. The product $FSO_2NMe_2$ is also an intermediate, and will further react with $Me_2NH$ to form $SO_2(NMe_2)_2$. This second reaction is slower than the first, but occurs whenever both $FSO_2NMe_2$ and $Me_2NH$ are present, so over time more $SO_2(NMe_2)_2$ will be obtained. $SO_2(NMe_2)_2$ was found in all of the Examples. At lower temperatures, $SO_2(NMe_2)_2$ formation was minimal. At higher temperatures, $SO_2(NMe_2)_2$ formation increased, and this increase is partly a function of time.

The time dependence is illustrated by comparing Examples 16 and 17. Both Examples 16 and 17 are identical in molar ratio (2.01:1), water content (60%), scale (10.34 moles $Me_2NH$), and temperature (40° C.). In example 16, an addition time of 21 minutes was made possible by addition of $SO_2F_2$ at elevated pressure, and a yield of 94% $FSO_2NMe_2$ obtained, with byproduct $SO_2(NMe_2)_2$ at a 2.4% yield. By contrast, in Example 17, an addition time of 152 minutes was used (for addition below atmospheric pressure), a yield of 86% $FSO_2NMe_2$ was obtained, and the yield of $SO_2(NMe_2)_2$ increased from 2.4% to 9.3%. Examples 16 and 17 clearly show the importance of minimizing addition time at 40° C., if $FSO_2NMe_2$ is the desired product.

The addition time raises issues with the size of batch reactors used in producing $FSO_2NMe_2$ in water. Since the reaction of $SO_2F_2$ with $Me_2NH$ is exothermic, larger reactors can have long addition times due to cooling power limits, and long residence times due to limits on gas absorption at the liquid surface. Longer lengths of time in a large reactor can produce more byproduct $SO_2(NMe_2)_2$ than with the shorter lengths of time expected in a smaller reactor.

At large scale, both addition and residence times can be minimized with a continuous process, wherein the gaseous and liquid reactants are combined under pressure at the head of a length of tubing immersed in a coolant bath, allowed to react, and the gas-free product stream continuously separated at the outlet. A gas-liquid continuous process of this nature is known to those skilled in the art and is well suited to the present Invention. Addition times can be very short in these embodiments of the Invention, and rapid temperature rise can occur at high pressure. Temperature rise in a continuous process in water can be reduced through the use of extended lengths of tubing at modest pressure, or increasing the water content of the process stream. $SO_2F_2$ can also be injected stepwise at one or more points downstream to achieve the same end.

Reaction in Water Below Atmospheric Pressure:

In some embodiments, the reaction may be conducted in water entirely below atmospheric pressure. In these embodiments, preferred water levels range from 35-60% w/w. At water levels below 60% w/w, pot temperatures must be kept low to keep the pressure down. The exact temperature range depends on the water content in the pot.

At a water level of 60% w/w, the reaction begins rapidly but slows down as it progresses, and the addition rate of $SO_2F_2$ must be reduced substantially towards completion, requiring 4.5-17 hours (h) (see examples 6, 8, 10, 11, 17, and 18). This problem is expected to be worse at higher water levels. The highest yield obtained with 60% w/w water at sub-atmospheric pressure was 93% after 4.5 h at −15° C., and a molar ratio of 2.03:1 (see example 10). A pot temperature as high as 44° C. can be maintained while keeping the pressure below atmospheric (see Example 18). The product stream rapidly separates into upper and lower layers at this water level.

At a water level of 49% w/w, the reaction proceeds much further towards completion before the addition rate must be reduced, and the reaction is completed in about 2 hours giving a 94% yield of $FSO_2NMe_2$ (see Example 4). A pot temperature of −3° C. must be maintained to keep the pressure below atmospheric. The product stream separates reasonably quickly into upper and lower layers at this water level.

At a water level of 39% w/w, the reaction proceeds to completion without a reduction in addition rate, and the reaction is completed in 2 hours giving a 96% yield of $FSO_2NMe_2$ (see Example 2). A pot temperature of −15° C. must be maintained to keep the pressure below atmospheric. The upper layer of the process stream was more dense and viscous at this water level than at higher water levels, and the product stream separated only slowly into upper and lower layers. Emulsified droplets persisted for some time in the separatory funnel.

While water levels below 39% w/w were not investigated, those skilled in the art will recognize that the emulsification problem can worsen as the water level drops further below 39% w/w.

Reaction in Water Above Atmospheric Pressure:

In some embodiments, the reaction may be conducted above atmospheric pressure. Operation in water above atmospheric pressure confers significant advantage and is preferred (see examples 3, 7, 9, 12, 13, 14, 15, 19, 20, and 21). Addition times have been reduced to as low as 19 minutes at 20° C., and a yield of 97% was obtained (see Example 14). A yield of 94% was obtained at 40° C., and a yield of 90% was obtained at 58° C. By use of a pressurized continuous process in water, both addition and residence times can be kept to a minimum.

Some of the conditions in which the present Invention may be performed are outlined in the table of Examples. Selected Examples are described in detail.

EXAMPLES

Examples 1-22 were conducted in a 2-liter stirred autoclave with an internal heat exchange coil.

General Procedure for Examples 1-21

An autoclave is charged with dimethylamine, cooled, and evacuated to constant static pressure. Sulfuryl fluoride is introduced into the head space with maximum agitation and cooling to maintain temperature. At the end of the reaction, the autoclave is vented, opened and the contents separated with a funnel. The lower layer is distilled under reduced pressure to give pure $FSO_2NMe_2$. Nearly pure $SO_2(NMe_2)_2$ remains in the still pot. The cold trap used for the reduced pressure distillations (all below $3 \times 10^{-3}$ MPa), inevitably contained some $FSO_2NMe_2$ which was not used for yield calculation.

Example 1: Reaction of $SO_2F_2$ with Anhydrous $Me_2NH$

A 2-liter autoclave was evacuated, cooled, and charged with anhydrous dimethylamine ($Me_2NH$, 366 g, 8.1 moles). The pot contents were stirred and sulfuryl fluoride (260 g, 2.54 moles) was introduced via a dip tube below the surface of the contents, maintaining a temperature between −14 and −28° C. and a pressure between 20 and 40 kPa, over a period of 97 minutes. The pot was then evacuated to 1.3 kPa while warming to −1° C. and left under static vacuum overnight. The next morning, the pot had risen to 1.7 kPa/6° C. The pot was vented through the dip tube and opened to reveal a mixture of sky-blue liquid and solid. No head space fouling was observed. Water (400 mL) was added and the dissolved contents separated into lower and upper layers. The lower layer was collected and distilled under reduced pressure to give the product $FSO_2NMe_2$ (294 g, 2.31 mole, 91%). Water content 147 ppm.

Example 2: Reaction of $SO_2F_2$ with 39% Aqueous $Me_2NH$ Below Atmospheric Pressure A 2-liter autoclave was evacuated, cooled, and charged with 60% aqueous $Me_2NH$ (655 g, 5.8 moles), followed by anhydrous $Me_2NH$ (349 g, 7.7 moles), cooled to −27° C., and evacuated to a static pressure of 5.3 kPa. The pot was stirred and $SO_2F_2$ (665 g, 6.5 moles) was added over 2 hours, at −15 to −20° C. and pressure below 44 kPa. At the end of the addition (−19° C.) the pressure dropped rapidly to 3 kPa. The pot was then warmed under modest dynamic vacuum to +20° C., opened, and the lower layer separated and fractionally distilled under reduced pressure to give the product (801 g, 6.3 moles, 96.9%). Water content 88 ppm.

Example 14: Reaction of $SO_2F_2$ with 60% Aqueous $Me_2NH$ Above Atmospheric Pressure A 2-liter autoclave was charged with 60% aqueous $Me_2NH$ (1.07 Kg, 9.5 moles), and evacuated with cooling to a static pressure of 4.8 kPa at −13° C. $SO_2F_2$ (482 g, 4.7 mole) was introduced to the stirred pot and the temperature rose quickly to the process level. Addition took place over 19 minutes in a pressure range of 0.27-0.44 MPa and a temperature range of 17-20° C. After addition was complete the pot was stirred with cooling for another 16 minutes and the pressure dropped to 1.4 kPa/9° C. The reactor was vented, opened, and the contents, a clear and colorless biphasic liquid, were separated and the lower layer distilled under reduced pressure to give the product (583 g, 4.6 mole, 97%). Water content 450 ppm.

Example 22: Reaction of $SO_2F_2$ with $Me_2NH$ in Acetonitrile

A 2-liter autoclave was charged with acetonitrile (1 liter), cooled to 2° C., and evacuated to constant static pressure ($4\times10^{-3}$ MPa). The reactor was charged with anhydrous $Me_2NH$ (91 g 2.02 moles) through a dip tube, and $SO_2F_2$ (103.8 g, 1.02 moles) introduced to the head space with stirring over 13 minutes at a pressure of $9\times10^{-2}$ MPa and a temperature of 15° C. At the end of the addition the pressure dropped rapidly to $1\times10^{-2}$ MPa. Stirring was continued for another 5 minutes, after which the reactor was evacuated to constant static pressure, infilled with nitrogen, and opened. The reactor contents, a clear, colorless liquid with very small amounts of solid crystals, were transferred to a rotary evaporator and the bulk of solvent removed. The biphasic liquid residue, free of solid, was partitioned with water (100 mL) and the cloudy lower layer separated from the upper layer (increased to 140 mL). The lower layer was then washed with brine (50 mL). The clear lower layer was separated from the cloudy brine layer and distilled under reduced pressure to give pure product $FSO_2NMe_2$ (63 g, 0.5 mole, 49%). 0.2 g semicrystalline residue remained in the still pot.

TABLE 1

| EXAMPLE | MOLES $HNMe_2$ | MOLES $SO_2F_2$ | $HNMe_2/SO_2F_2$ | $H_2O$ w/w | T (MAX) | T (MEAN) | T (END) | P (END) (MPa) |
|---|---|---|---|---|---|---|---|---|
| 1 | 8.12 | 2.54 | 3.19 | 0% | −13° C. | −15° C. | −26° C. | 1.7E−03 |
| 2 | 13.55 | 6.52 | 2.08 | 39% | −10° C. | −15° C. | −28° C. | 4.9E−03 |
| 3 | 7.37 | 3.67 | 2.00 | 77% | 31° C. | 30° C. | 29° C. | 2.3E−02 |
| 4 | 11.50 | 5.07 | 2.27 | 49% | 1° C. | −3° C. | −8° C. | 7.3E−03 |
| 5 | 11.32 | 7.26 | 1.56 | 49% | 0° C. | −5° C. | −4° C. | 3.4E−02 |
| 6 | 8.15 | 4.15 | 1.96 | 60% | −3° C. | −4° C. | −6° C. | 4.7E−03 |
| 7 | 8.10 | 5.22 | 1.55 | 60% | −3° C. | −4° C. | −15° C. | 2.5E−01 |
| 8 | 8.29 | 3.96 | 2.10 | 60% | −15° C. | −19° C. | −26° C. | 6.7E−03 |
| 9 | 12.42 | 6.19 | 2.01 | 60% | 1° C. | −3° C. | −27° C. | 3.5E−03 |
| 10 | 8.87 | 4.38 | 2.03 | 60% | −14° C. | −15 C. | −14° C. | 3.6E−03 |
| 11 | 8.52 | 3.86 | 2.21 | 60% | 1° C. | −4° C. | 9° C. | 1.1E−02 |
| 12 | 9.87 | 4.92 | 2.01 | 60% | 11° C. | 10° C. | 10° C. | 3.0E−02 |
| 13 | 8.15 | 3.88 | 2.10 | 60% | 26° C. | 18° C. | 10° C. | 2.8E−01 |
| 14 | 9.49 | 4.72 | 2.01 | 60% | 20° C. | 20° C. | 9° C. | 1.4E−02 |
| 15 | 9.06 | 4.51 | 2.01 | 60% | 33° C. | 30° C. | 10° C. | 1.6E−02 |
| 16 | 10.34 | 5.15 | 2.01 | 60% | 43° C. | 40° C. | 37° C. | 1.8E−02 |
| 17 | 10.34 | 5.14 | 2.01 | 60% | 43° C. | 40° C. | 37° C. | 4.8E−02 |
| 18 | 8.32 | 3.66 | 2.28 | 60% | 45° C. | 44° C. | 9° C. | 6.0E−02 |
| 19 | 10.10 | 4.98 | 2.03 | 60% | 61° C. | 58° C. | 19° C. | 3.1E−02 |
| 20 | 4.98 | 2.27 | 2.19 | 60% | 82° C. | 79° C. | 18° C. | 5.0E−02 |
| 21 | 8.08 | 4.26 | 1.90 | 60% | 106° C. | 101° C. | 19° C. | 4.0E−02 |

| EXAMPLE | P (MAX) (MPa) | ADD TIME (h) | TOTAL (h) | YIELD $FSO_2NMe_2$ | YIELD $SO_2(NMe_2)_2$ |
|---|---|---|---|---|---|
| 1 | 4.1E−02 | 1.68 | 1.68 | 91% | 0.1% |
| 2 | 9.3E−02 | 1.97 | 3.0 | 96% | 0.2% |
| 3 | 6.9E−01 | 1.32 | 1.3 | 85% | 3.4% |
| 4 | 8.4E−02 | 1.25 | 2.0 | 94% | 0.7% |
| 5 | 7.5E−02 | 18.00 | 18.0 | 78% | 0.4% |
| 6 | 9.3E−02 | 12.53 | 12.5 | 79% | 1.6% |
| 7 | 5.5E−01 | 1.13 | 1.5 | 77% | 0.1% |
| 8 | 9.7E−02 | 8.10 | 9.0 | 89% | n.r. |
| 9 | 5.5E−01 | 3.17 | 3.6 | 96% | 0.8% |
| 10 | 8.8E−02 | 4.33 | 4.5 | 93% | 0.5% |
| 11 | 9.6E−02 | 3.80 | 16.7 | 90% | 2.8% |
| 12 | 1.9E−01 | 2.27 | 2.3 | 97% | 0.6% |

TABLE 1-continued

| | | | | | |
|---|---|---|---|---|---|
| 13 | 6.9E−01 | 1.70 | 13.4 | 89% | 1.7% |
| 14 | 4.4E−01 | 0.32 | 0.52 | 97% | 0.7% |
| 15 | 4.4E−01 | 0.57 | 0.6 | 95% | 0.9% |
| 16 | 6.9E−01 | 0.35 | 0.5 | 94% | 2.4% |
| 17 | 1.0E−01 | 2.53 | 14.5 | 86% | 9.3% |
| 18 | 9.7E−02 | 4.00 | 15.0 | 75% | 17.4% |
| 19 | 4.5E−01 | 0.42 | 2.0 | 90% | 5.2% |
| 20 | 6.2E−01 | 0.20 | 1.1 | 83% | 9.9% |
| 21 | 1.4E+00 | 0.13 | 0.4 | 79% | 8.2% |

Although the subject matter has been described in terms of exemplary embodiments, it is not limited thereto. Rather, the appended claims should be construed broadly, to include other variants and embodiments, which may be made by those skilled in the art.

What is claimed is:

1. A method, comprising:
    reacting dimethylamine (Me$_2$NH) with sulfuryl fluoride (SO$_2$F$_2$) in an aqueous solvent to form at least a first liquid phase comprising N-(fluorosulfonyl) dimethylamine (FSO$_2$NMe$_2$), tetramethylsulfamide (SO$_2$(NMe$_2$)$_2$), or a mixture thereof; and
    isolating FSO$_2$NMe$_2$ or SO$_2$(NMe$_2$)$_2$ from the first phase.

2. The method of claim 1, wherein the solvent is a mixture comprising water and a second solvent.

3. The method of claim 2, wherein the second solvent is selected from the group consisting of dichloromethane, diethyl ether, tetrahydrofuran, 2-methyltetrahydrofuran, methylcyclopentyl ether, methyl tert-butyl ether, acetonitrile, propionitrile, butyronitrile, toluene, and any combination thereof.

4. The method of claim 1, further comprising separating a second phase from the first phase, wherein the second phase comprises dimethylamine hydrofluoride (Me$_2$NH$_2$F).

5. The method of claim 4, wherein the second phase is in a liquid form that is less dense than the first phase or the second phase is a solid form.

6. The method of claim 1, wherein FSO$_2$NMe$_2$ or SO$_2$(NMe$_2$)$_2$ is isolated by distilling the first phase, optionally under a reduced pressure.

7. The method of claim 1, further comprising separating FSO$_2$NMe$_2$ and SO$_2$(NMe$_2$)$_2$, wherein the first liquid phase comprises a mixture of FSO$_2$Me$_2$ and SO$_2$(NMe$_2$)$_2$.

8. The method of claim 7, wherein FSO$_2$NMe$_2$ is a resulting product having a yield of 75% or higher.

9. The method of claim 1, wherein water is present in an amount between about 35% and about 80% by weight before SO$_2$F$_2$ is added.

10. The method of claim 1, wherein Me$_2$NH is reacted with SO$_2$F$_2$ at a molar ratio of Me$_2$NH to SO$_2$F$_2$ between about 0.1:1 and about 4:1.

11. The method of claim 1, wherein Me$_2$NH is reacted with SO$_2$F$_2$ at a molar ratio of Me$_2$NH to SO$_2$F$_2$ between about 2.00:1 and about 2.09:1.

12. The method of claim 1, wherein Me$_2$NH is reacted with SO$_2$F$_2$ at a molar ratio of Me$_2$NH to SO$_2$F$_2$ being 4:1 or higher.

13. The method of claim 1, wherein Me$_2$NH is reacted with SO$_2$F$_2$ at a temperature between about −30° C. and about 110° C.

* * * * *